US010271939B2

(12) United States Patent
Hazama et al.

(10) Patent No.: US 10,271,939 B2
(45) Date of Patent: Apr. 30, 2019

(54) TREATMENT METHOD AND MEDICAL APPARATUS

(71) Applicant: Terumo Kabushiki Kaisha, Tokyo (JP)

(72) Inventors: Kenichi Hazama, Kanagawa (JP); Yoshiyuki Hara, Fujinomiya (JP); Junichi Kobayashi, Fuji (JP); Kenji Watanabe, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 2 days.

(21) Appl. No.: 15/424,162

(22) Filed: Feb. 3, 2017

(65) Prior Publication Data

US 2017/0224465 A1  Aug. 10, 2017

(30) Foreign Application Priority Data

Feb. 10, 2016 (JP) .................. 2016-024068

(51) Int. Cl.
*A61F 2/04* (2013.01)
*A61F 2/20* (2006.01)
*A61B 17/00* (2006.01)
*A61B 17/24* (2006.01)
*A61M 25/00* (2006.01)
*A61M 25/01* (2006.01)
*A61M 25/09* (2006.01)

(52) U.S. Cl.
CPC ............... *A61F 2/04* (2013.01); *A61B 17/24* (2013.01); *A61M 25/0026* (2013.01); *A61B 2017/00809* (2013.01); *A61F 2/20* (2013.01); *A61F 2002/044* (2013.01); *A61F 2002/046* (2013.01); *A61F 2210/009* (2013.01); *A61F 2220/0016* (2013.01); *A61M 25/0043* (2013.01); *A61M 25/0136* (2013.01); *A61M 25/09041* (2013.01); *A61M 2025/004* (2013.01)

(58) Field of Classification Search
USPC .............................................. 623/23.63–23.7
See application file for complete search history.

(56) References Cited

U.S. PATENT DOCUMENTS 4,995,388 A * 2/1991 Brain .................... A61M 16/04
128/207.14

FOREIGN PATENT DOCUMENTS

| JP | 2004-538060 | 12/2004 |
| JP | 2007-267999 | 10/2007 |
| JP | 2009-520559 | 5/2009 |
| WO | WO 03/011179 | 2/2003 |
| WO | WO 2007-072469 | 6/2007 |

* cited by examiner

*Primary Examiner* — Yashita Sharma
(74) *Attorney, Agent, or Firm* — Jason H. Vick; Sheridan Ross, PC

(57) ABSTRACT

Provided is a treatment method and medical apparatus for preventing an object that becomes a causative agent causing pathogenesis of aspiration pneumonitis from invading a lung The treatment method includes a disposing step of disposing a first instrument, which allows the object that becomes a causative agent of aspiration pneumonitis to move from an esophagus to a stomach and suppresses movement of the object from the stomach to a larynx, in the esophagus and disposing a second instrument, which suppresses the object from invading the lung, in at least the larynx.

5 Claims, 10 Drawing Sheets

TREATMENT METHOD AND MEDICAL APPARATUS

CROSS REFERENCE TO RELATED APPLICATIONS

The present application claims the benefit of priority, under 35 U.S.C. § 119(e), to Japanese Application No. 2016-024068, filed Feb. 10, 2016, entitled "Treatment Method and Apparatus," the entire disclosure of which is incorporated herein by reference in its entirety, for all that it teaches and for all purposes.

TECHNICAL FIELD

The present invention relates to a treatment method for preventing an object that becomes a causative agent causing pathogenesis of aspiration pneumonitis from invading a lung, and a medical apparatus for preventing an object that becomes a causative agent causing pathogenesis of aspiration pneumonitis from invading a lung.

BACKGROUND

Aspiration pneumonitis is a disease occurring due to bacteria or the like which adhere to food, saliva, or the like when the food, the saliva, or the like enters the inside of a lung through the trachea. In addition, recently, it has become known that aspiration pneumonitis occurs similarly when foreign bodies such as gastric juice which have flowed backward from the stomach to the esophagus enter the inside of the lung through the trachea during sleep. Foreign bodies such as food are likely to enter the inside of a lung of aged people or the like due to a deteriorated swallowing function, and resisting power for discharging (expectorating) the foreign bodies which have entered the inside of the lung is weak. Therefore, in accordance with aging of the population, the number of patients suffering from pathogenesis of aspiration pneumonitis tends to increase year after year.

For example, Japanese Patent Application Nos. JP-A-2007-267999, JP-T-2009-520559, and/or JP-T-2004-538060 disclose methods in which a medical instrument such as an implantable device and a valve for inhibiting gastric juice or the like from flowing backward from the stomach to the esophagus indwells in the esophagus, the stomach, or the like, to prevent pathogenesis of reflux esophagitis caused by gastroesophageal reflux disease occurring when the gastric juice flows backward into the esophagus.

SUMMARY

Technical Problem

When the above-described method in which a medical instrument such as an implantable device and a valve indwells is employed, gastric juice or the like can be prevented from flowing backward from the stomach to the esophagus. Therefore, pathogenesis of aspiration pneumonitis occurring due to back-flow of gastric juice can be prevented.

However, pulmonary aspiration occurring when orally ingested food or the like invades the inside of the trachea cannot be prevented. In addition, in a case where a bit of gastric juice flows backward from the stomach to the larynx for instance, the possibility that the gastric juice invades the inside of a lung via the esophagus and the trachea cannot be excluded. Therefore, even if the implantable device, the valve, or the like inhibiting gastric juice or the like from flowing backward from the stomach to the larynx is utilized, it is considered difficult to sufficiently prevent pathogenesis of aspiration pneumonitis.

Therefore, the embodiments herein aim to provide a treatment method for preventing an object that becomes a causative agent causing pathogenesis of aspiration pneumonitis from invading a lung, and a medical apparatus for preventing an object that becomes a causative agent causing pathogenesis of aspiration pneumonitis from invading a lung.

Solution to the Problem

According to embodiments herein, a treatment method for preventing an object that becomes a causative agent of aspiration pneumonitis from invading a lung includes a disposing step of disposing a first instrument, which allows the object to move from an esophagus to a stomach and suppresses movement of the object from the stomach to a larynx, in the esophagus and disposing a second instrument, which suppresses the object from invading the lung, in at least the larynx.

According to the embodiments herein, a medical apparatus for preventing an object that becomes a causative agent of aspiration pneumonitis from invading a lung includes a first instrument that is disposed in the esophagus to allow the object to move from an esophagus to a stomach and to suppress movement of the object from the stomach to a larynx, and a second instrument that is disposed in at least the larynx to suppress the object from invading the lung.

Advantageous Effect

According to the treatment method of the embodiments herein, due to the first instrument disposed in the esophagus, gastric juice or the like can be prevented from flowing backward from the stomach to the larynx. Moreover, due to the second instrument disposed in the larynx, pulmonary aspiration of food, saliva, or the like invading a lung via the larynx and the trachea can be prevented from occurring. Therefore, pathogenesis of aspiration pneumonitis can be favorably prevented.

According to the medical apparatus of the embodiments herein, due to the first instrument disposed in the esophagus, gastric juice or the like can be prevented from flowing backward from the stomach to the larynx. Moreover, due to the second instrument disposed in the larynx, pulmonary aspiration of food, saliva, or the like invading a lung via the trachea can be prevented from occurring. Therefore, pathogenesis of aspiration pneumonitis can be favorably prevented.

DETAILED DESCRIPTION

Hereinafter, with reference to each of the drawings, embodiments will be described. Note that, for the convenience of description, there are cases where the dimensional ratios of the drawings are exaggerated and are different from the actual ratios.

Figure 2:
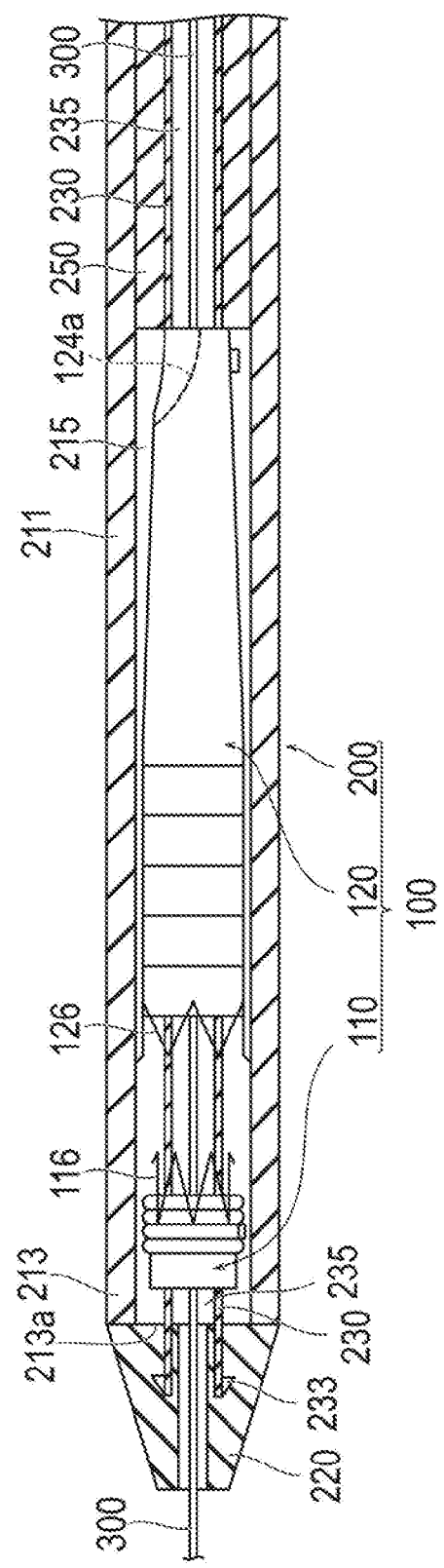
FIG. 2 is a cross-sectional view of an embodiment of a portion 2A along an axial direction illustrated in FIG. 1.
Figure 3A:
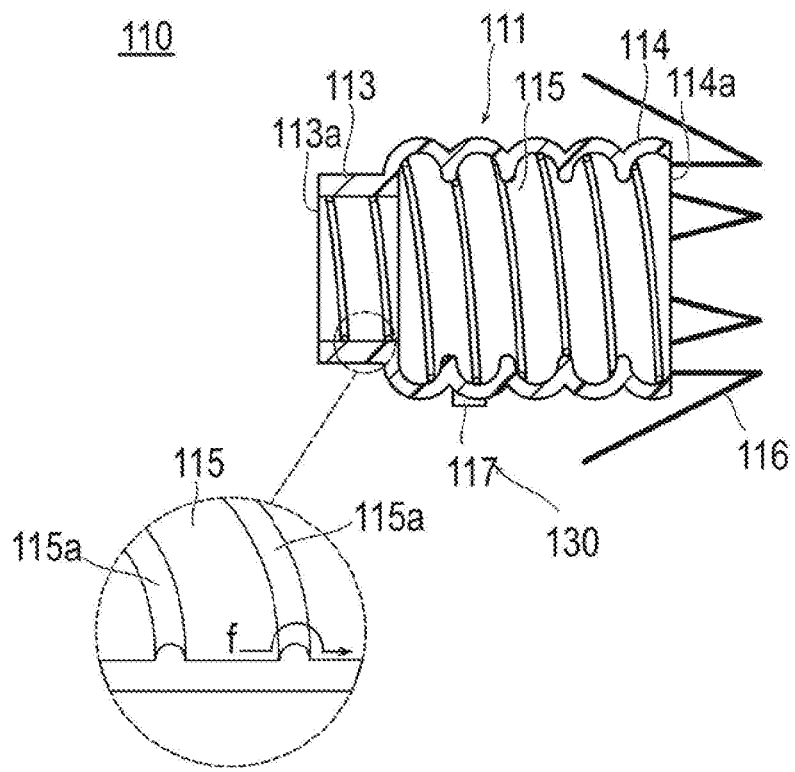
FIG. 3A is a cross-sectional view of an embodiment of a first instrument provided in the medical apparatus.
Figure 3B:
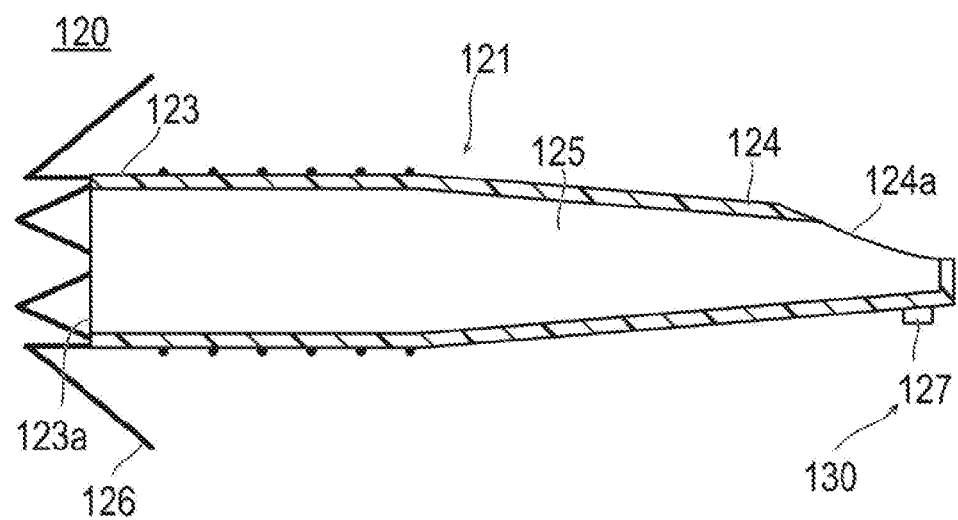
FIG. 3B is a cross-sectional view of an embodiment of a second instrument provided in the medical apparatus.
Figure 4:
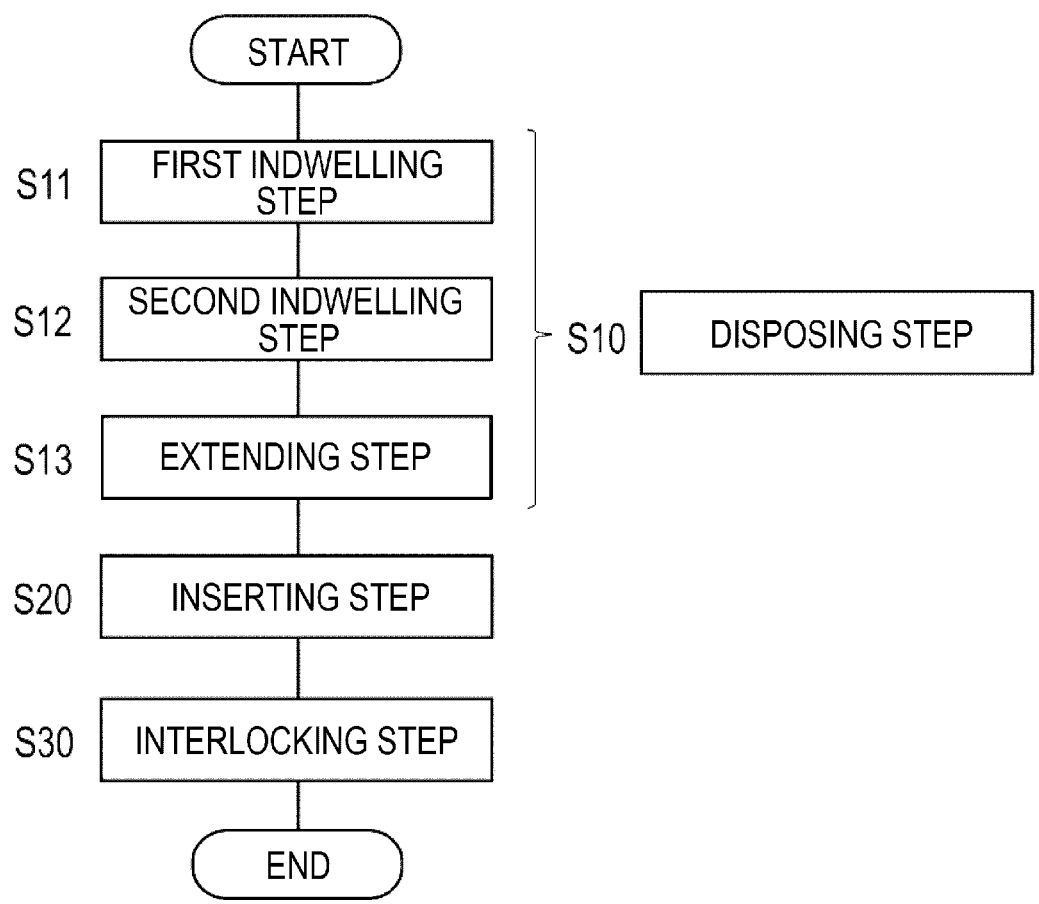
FIG. 4 is a flowchart of an embodiment illustrating each process of a treatment method.
Figure 5:
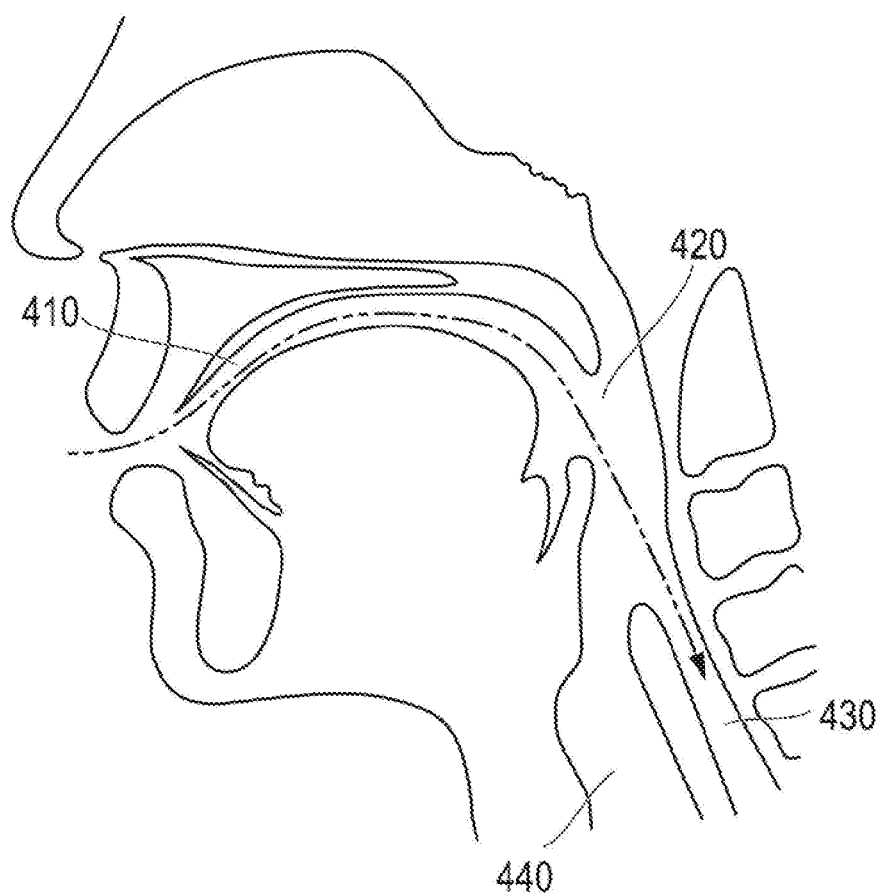
FIG. 5 is a view schematically illustrating an embodiment of a part of a living body to which the treatment method is applied.

FIGS. 1 to 3B are views illustrating the configuration of each portion of a medical apparatus 100. FIG. 4 is a flow chart illustrating each process of a treatment method. FIG. 5 is a view schematically illustrating a part of a living body to which the treatment method is applied. FIGS. 6A to 10B are cross-sectional views schematically illustrating the treatment method.

Figure 10A:
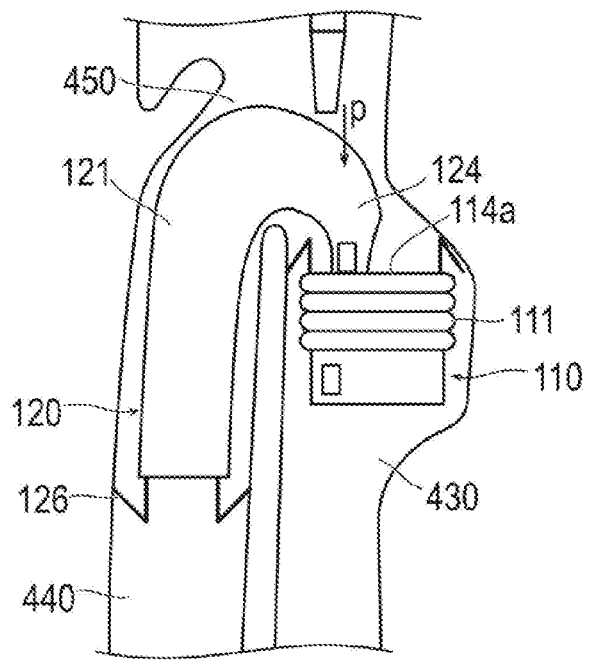
FIGS. 10A and 10B are cross-sectional views schematically illustrating an embodiment of the treatment method.
Figure 10B:
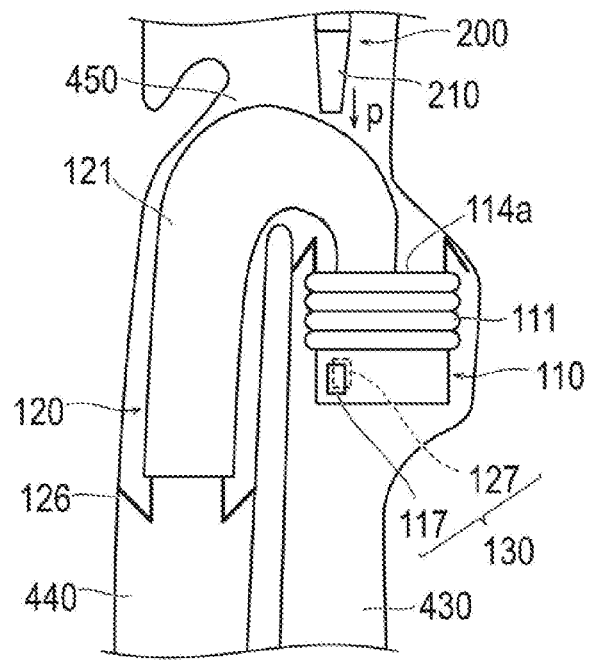

As illustrated in FIGS. 10A and 10B, the treatment method is a method in which a predetermined first instrument 110 indwells in an esophagus 430 and a predetermined second instrument 120 indwells in a larynx (including the vocal cord and the epiglottis) 450 to suppress an object that becomes a causative agent of aspiration pneumonitis from invading a lung via the larynx 450 and a trachea 440, thereby preventing pathogenesis of aspiration pneumonitis. As the object that becomes a causative agent of aspiration pneumonitis, for example, it is possible to exemplify orally taken food, saliva generated inside the oral cavity, various types of secretion generated inside the nasal cavity, and gastric juice generated inside the stomach. However, the object that becomes a target to be prevented from invading a lung by the treatment method is not limited to the above-described examples. The object widely includes various types of objects and substances which can cause pathogenesis of aspiration pneumonitis by invading a lung.

Figure 1:
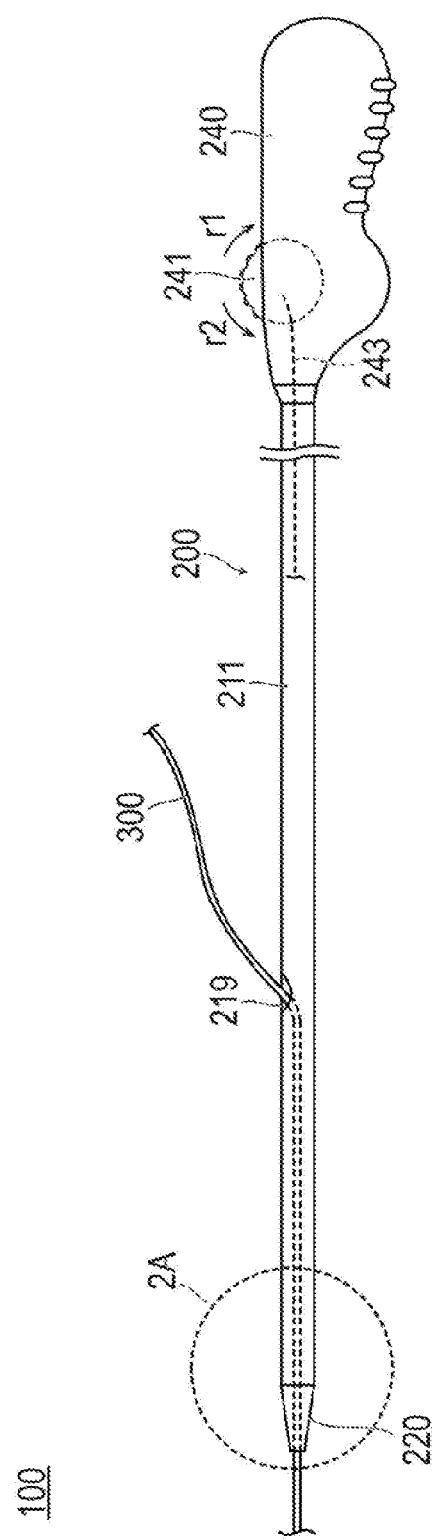
FIG. 1 is a view illustrating an embodiment of a medical apparatus.

First, with reference to FIGS. 1 to 3B, description will be given regarding the medical apparatus 100 which is favorably used in the treatment method. FIG. 1 illustrates the overall configuration of the medical apparatus 100. FIG. 2 illustrates an enlarged cross-sectional view of a portion 2A illustrated in FIG. 1. FIGS. 3A and 3B illustrate a cross-sectional view of the first instrument 110 and the second instrument 120 along an axial direction.

As illustrated in FIGS. 1 and 2, the medical apparatus 100 has a catheter 200, the first instrument 110 which is delivered to the inside of the esophagus 430 through the catheter 200, and the second instrument 120 which is delivered to the inside of the trachea 440 through the catheter 200.

Note that, in each of the first instrument 110, the second instrument 120, and the catheter 200, a side inserted into a living body will be referred to as "distal side", the opposite side of the distal side will be referred to as "proximal side", and an extending direction of a shaft 211 included in the catheter 200 will be referred to as the axial direction.

The catheter 200 will now be described.

As illustrated in FIGS. 1 and 2, the catheter 200 has the shaft (outer sheath) 211 extending in the axial direction, a distal tip 220 disposed at the distal end of the shaft 211, and hand operation unit 240 disposed at the proximal end of the shaft 211.

As illustrated in FIG. 2, a lumen 215 accommodating the first instrument 110 and the second instrument 120 is placed inside the shaft 211. The lumen 215 accommodates the first instrument 110 and the second instrument 120 in order from the distal side.

An inner shaft 230 is inserted into the shaft 211 along the axial direction. A guide lumen 235 through which a guide member 300 adopted when the catheter 200 is inserted into the esophagus 430 or a larynx 450 of a living body can be inserted is formed inside the inner shaft 230. The guide lumen 235 communicates with an opening portion 219, which is formed in the middle of the shaft 211, in the axial direction (refer to FIG. 1). As illustrated in FIG. 2, the guide member 300 is inserted through the opening portion 219 and is inserted through the inner shaft 230, thereby being able to protrude toward the distal side through the distal tip 220.

As the guide member 300, for example, known image-capturing means (endoscope or the like) or a known guide wire can be adopted without being particularly limited thereto. However, while performing the procedure in which the catheter 200 is used, an endoscope can be utilized as the guide member 300 to facilitate observing the inside of the esophagus 430 or the larynx 450.

As illustrated in FIG. 2, a fixing portion 233 is provided in a distal portion of the inner shaft 230 and is fixed to the distal tip 220. For example, the fixing portion 233 can be formed to have a shape protruding radially outward. The fixing portion 233 is fixed to the distal tip 220 in a hooked manner.

As illustrated in FIG. 1, the hand operation unit 240 of the catheter 200 is provided with a rotary wheel 241. In a simplified view, the rotary wheel 241 is connected to the shaft 211 via a pulling member 243 such as a pulling wire. When the rotary wheel 241 is operated to rotate in a direction r1 (clockwise direction), the pulling member 243 is pulled toward the proximal side and the shaft 211 moves toward the proximal side. In addition, when the rotary wheel 241 is operated to rotate in a direction r2 (counterclockwise direction), the pulling member 243 is pushed toward the distal side and the shaft 211 moves toward the distal side.

When the shaft 211 moves toward the proximal side in response to the above-described operation, the first instrument 110 and the second instrument 120 accommodated inside the shaft 211 are released from the lumen 215 of the shaft 211. In addition, after the first instrument 110 and the second instrument 120 are released from the lumen 215 of the shaft 211, when the shaft 211 is operated to be pushed toward the distal side, the inner shaft 230 can return to a state of being covered with the shaft 211.

As illustrated in FIG. 2, inside the lumen 215 of the shaft 211, a predetermined support member 250 is disposed on the proximal side of the second instrument 120. The support member 250 is provided to prevent the second instrument 120 from moving to the proximal side in association with movement of the shaft 211 when the shaft 211 is moved.

Note that, each portion of the catheter 200 can be configured by using a resin material, a metal material, or the like which is generally adopted in catheters and the like in the medical field.

The first instrument 110 will now be described.

As illustrated in FIG. 3A, the first instrument 110 has a hollow main body portion (first main body portion) 111, and a first expansion portion 116 which is attached to the outer circumferential surface of a proximal portion 114 of the main body portion 111.

The main body portion 111 has a distal end opening portion 113a formed in a distal portion 113, a proximal end opening portion 114a formed in the proximal portion 114, and a lumen 115 communicating with the distal end opening portion 113a and the proximal end opening portion 114a.

As illustrated in the enlarged view in FIG. 3A, a projection portion 115a spirally extending along the circumferential direction of the inner surface of the main body portion 111 is formed on the inner surface thereof. The projection portion 115a functions to prevent gastric juice f or the like from flowing backward along the inner surface of the main body portion 111 while the first instrument 110 is in an indwelling state inside the esophagus 430 (refer to FIG. 10B). Note that, as illustrated in FIG. 3A, the projection portion 115a may be formed throughout the entirety of the main body portion 111 in the axial direction or may be formed only in a portion of the main body portion 111. In addition, for example, a configuration other than the projection portion 115a (for example, a recessed groove portion) may be formed inside the lumen 115 to prevent the gastric juice for the like from flowing backward.

A portion of the main body portion 111 on the proximal portion 114 side is configured to be expandingly deformed in the radial direction (vertical direction in FIG. 3A) in response to the expandingly deformed first expansion portion 116. Note that, FIG. 3A illustrates the first expansion portion 116 and the main body portion 111 in a state of being released from the shaft 211 of the catheter 200 and being expandingly deformed.

The first expansion portion 116 is configured to be made of a self-expandable member expandingly deformed radially outward from the main body portion 111 in response to release from the lumen 215 of the catheter 200. As the self-expandable member, for example, a super-elastic alloy such as a nickel-titanium alloy, a polymer material, and/or other metal materials can be used.

As the configuration material of the main body portion 111, for example, it is preferable to adopt a biocompatible material so that a load applied to the esophagus 430 can be reduced while being in an indwelling state inside the esophagus 430. In addition, for example, the skeleton of the main body portion 111 can be formed to have a configuration similar to that of a known self-expandable-type stent, and the main body portion 111 can be configured by utilizing porous woven fabric, a resin film, or the like which is disposed to partially cover the skeleton.

The second instrument 120 will now be described.

As illustrated in FIG. 3B, the second instrument 120 has a hollow main body portion (second main body portion) 121, and a second expansion portion 126 which is attached to the outer circumferential surface of a distal portion 123 of the main body portion 121.

The main body portion 121 has a distal end opening portion 123a formed in the distal portion 123, a proximal end opening portion 124a formed by obliquely cutting a proximal portion 124, and a lumen 125 communicating with the distal end opening portion 123a and the proximal end opening portion 124a.

In the main body portion 121, the inner diameter and the outer diameter on the proximal portion 124 side are formed to be smaller than those on the distal portion 123 side. In addition, the main body portion 121 is configured to be contractively deformable in the axial direction. The distal portion 123 of the main body portion 121 is configured to be expandingly deformed in the radial direction (vertical direction in FIG. 3B) in response to the expandingly deformed second expansion portion 126. Note that, FIG. 3B illustrates the second expansion portion 126 and the main body portion 121 in a state of being released from the shaft 211 of the catheter 200 and being expandingly deformed.

Similar to the first expansion portion 116, the second expansion portion 126 is configured to be made of a self-expandable member expandingly deformed radially outward from the main body portion 121 in response to release from the lumen 215 of the catheter 200. Any material used for the first expansion portion 116 can be adopted for the second expansion portion 126.

The main body portion 121 can be provided with ventilation characteristics to allow gas such as air to move via the trachea 440 and suppresses circulation of taken food or the like while being in an indwelling state inside the larynx 450 and the trachea 440. As the configuration of the main body portion 121 having such functions, for example, the skeleton of the main body portion 121 can be formed to have a configuration similar to that of a known self-expandable-type stent and can be configured by utilizing porous woven fabric, a resin film, or the like which is disposed to partially cover the skeleton.

The first instrument 110 and the second instrument 120 are provided with interlocking means 130 that interlocks the instruments 110 and 120 with each other in a state where the first instrument 110 indwells in the esophagus 430 and the second instrument 120 indwells in the larynx 450 and the trachea 440 (refer to FIG. 10B).

The interlocking means 130 is configured to have a first magnet 117 disposed on the outer surface of the first instrument 110, and a second magnet 127 disposed on the outer surface of the second instrument 120. When the first magnet 117 and the second magnet 127 are brought to be close to each other, magnetic force acts between the first magnet 117 and the second magnet 127, and the first magnet 117 and the second magnet 127 are interlocked with each other. Note that, the interlocking means 130 may have a configuration other than the magnets as long as the first instrument 110 and the second instrument 120 can be interlocked with each other. For example, the interlocking means 130 can be configured to perform interlocking through mechanical fitting or can be configured to be a separate member independent from the first instrument 110 and the second instrument 120.

As illustrated in FIG. 2, the first instrument 110 and the second instrument 120 are accommodated inside the lumen 215 provided in the catheter 200 when being introduced into a living body. While being accommodated inside the lumen 215, the first expansion portion 116 of the first instrument 110 and the second expansion portion 126 of the second instrument 120 maintain a contraction state by being pressed by the inner wall of the shaft 211 from the outer circumferential side.

The first instrument 110 is held by the inner shaft 230 in a state where the inner shaft 230 is inserted through the lumen 115 of the main body portion 111. When the shaft 211 moves toward the proximal side, first instrument 110 is prevented from moving to the proximal side due to friction force acting between the inner surface of the first instrument 110 and the outer surface of the inner shaft 230, and only the shaft 211 moves toward the proximal side. Then, when a distal end opening portion 213a of the shaft 211 moves toward the proximal side closer than the proximal end of the first instrument 110, the first instrument 110 is released from the shaft 211. The first expansion portion 116 of the first instrument 110 is expandingly deformed in response to the release thereof. Similarly, the second expansion portion 126 is released from the shaft 211 when the distal end opening portion 213a of the shaft 211 moves toward the proximal side closer than the proximal end of the second instrument 120. The second expansion portion 126 of the second instrument 120 is expandingly deformed in response to the release thereof.

Note that, arbitrary places of the first instrument 110 and the second instrument 120 can have X-ray contrast properties. For example, the first expansion portion 116, the second expansion portion 126, and the like can have X-ray contrast properties. When the first instrument 110 and the second instrument 120 have X-ray contrast properties, indwelling can proceed under an X-ray image-capturing condition.

Subsequently, with reference to FIGS. 4 to 10B, the treatment method according to embodiments herein will be described.

As illustrated in FIG. 4, in brief, the treatment method has a disposing step (S10), an inserting step (S20), and an interlocking step (S30). In addition, the disposing step (S10) can have a first indwelling step (S11), a second indwelling step (S12), and an extending step (S13). Hereinafter, each of the steps will be described.

In the disposing step (S10), the first instrument 110 is disposed in the esophagus 430, and the second instrument 120 is disposed in the larynx 450 and the trachea 440. Specifically, in the disposing step (S10), the first indwelling step (S11) of causing the catheter 200 to be inserted into the esophagus 430 and the first instrument 110 to indwell inside the esophagus 430 is performed. Subsequently, the second indwelling step (S12) of causing the catheter 200 to be inserted into the larynx 450 and the trachea 440 and the second instrument 120 to indwell inside the larynx 450 and the trachea 440 is performed. Then, the extending step (S13) of causing the second instrument 120 to extend across from the larynx 450 and the trachea 440 to the esophagus 430 is performed.

With reference to FIG. 5, for example, the catheter 200 can be delivered to the inside of the esophagus 430 via an oral cavity 410 and a pharynx 420 in order. However, instead of the oral cavity 410, the catheter 200 can be delivered to the inside of the esophagus 430 via the nasal cavity side.

Figure 6A:
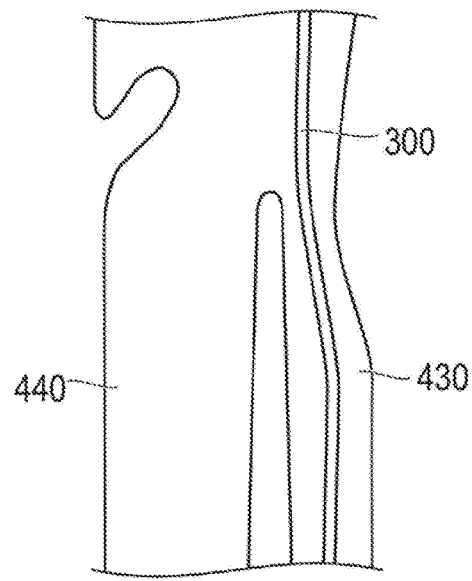
FIGS. 6A and 6B are cross-sectional views schematically illustrating an embodiment of the treatment method.

As illustrated in FIG. 6A, the guide member 300 is inserted into the esophagus 430 along the above-described route. The disposing step (S10) can promptly and easily proceed when image-capturing is performed by utilizing an endoscope as the guide member 300.

Figure 6B:
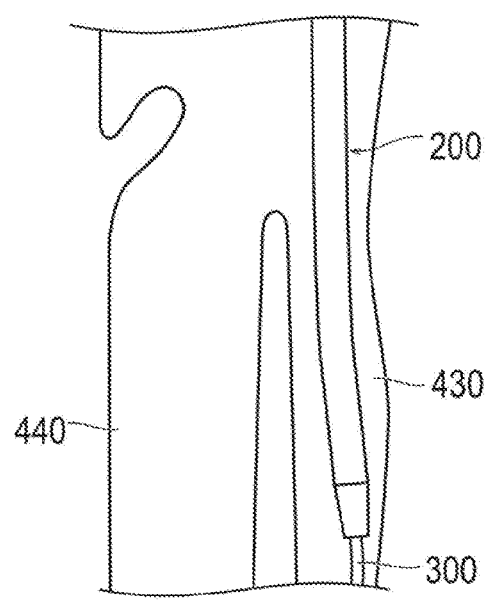

Subsequently, as illustrated in FIG. 6B, the catheter 200 is inserted into the esophagus 430 along the guide member 300.

Figure 7A:
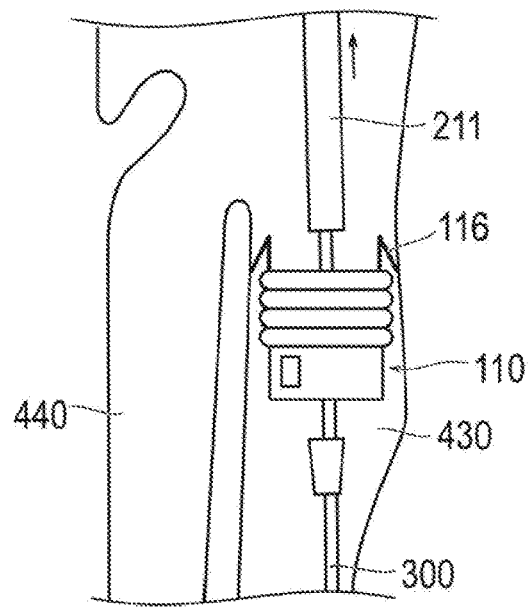
FIGS. 7A and 7B are cross-sectional views schematically illustrating an embodiment of the treatment method.

Subsequently, as illustrated in FIG. 7A, the first instrument 110 is released by moving the shaft 211 of the catheter 200 toward the proximal side. The first expansion portion 116 of the first instrument 110 is expandingly deformed in response to the release of the first instrument 110 and causes holding force to act on the inner wall of the esophagus 430. The first instrument 110 maintains an indwelling state in the esophagus 430 via the first expansion portion 116.

Figure 7B:
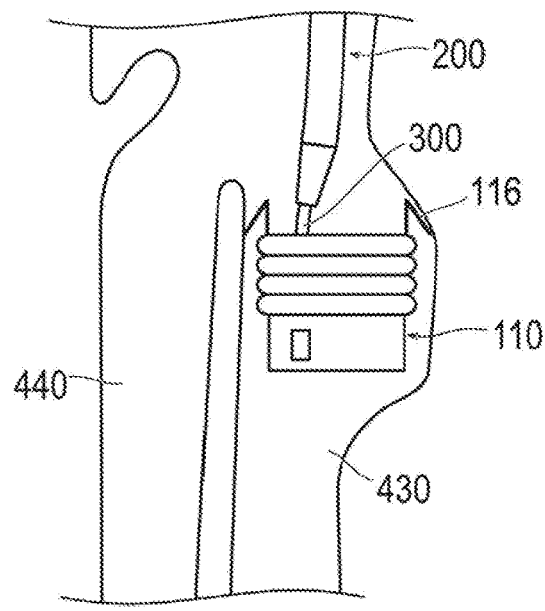

Subsequently, as illustrated in FIG. 7B, the guide member 300 and the catheter 200 are moved toward the proximal side. In this case, the guide member 300 and the catheter 200 may be temporarily collected outside a living body or may shift to the next stage without being taken out from the living body.

Figure 8A:
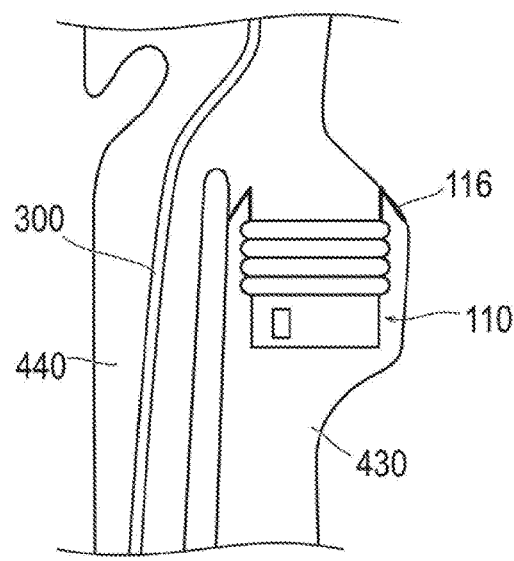
FIGS. 8A and 8B are cross-sectional views schematically illustrating an embodiment of the treatment method.

For example, in a case where the guide member 300 and the catheter 200 are temporarily collected outside the living body, the guide member 300 is delivered to the inside of the trachea 440 via the oral cavity 410 and the pharynx 420 in order, as illustrated in FIG. 8A.

Figure 8B:
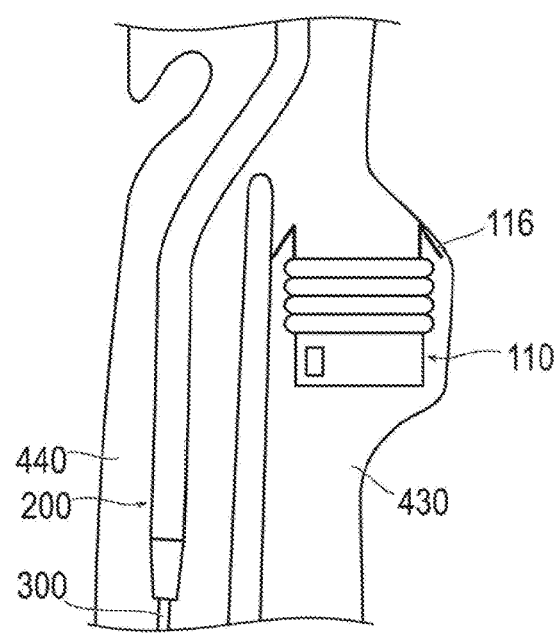

Subsequently, as illustrated in FIG. 8B, the catheter 200 is inserted into the trachea 440 along the guide member 300.

Figure 9A:
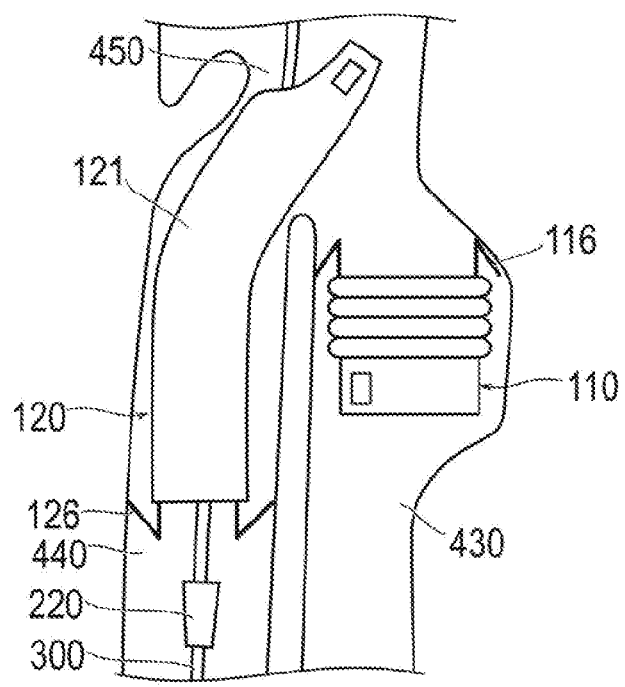
FIGS. 9A and 9B are cross-sectional views schematically illustrating an embodiment of the treatment method.

Subsequently, as illustrated in FIG. 9A, the second instrument 120 is released by moving the shaft 211 of the catheter 200 toward the proximal side. The second expansion portion 126 of the second instrument 120 is expandingly deformed in response to the release of the second instrument 120 and exerts a holding force on the inner wall of the trachea 440. The main body portion 121 of the second instrument 120 maintains an indwelling state in the larynx 450 and the trachea 440 via the second expansion portion 126.

Figure 9B:
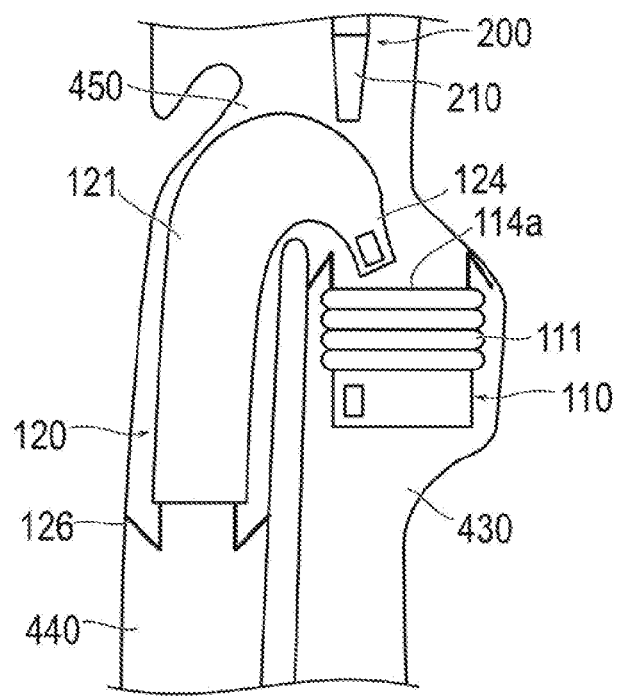

Subsequently, as illustrated in FIG. 9B, the guide member 300 and the catheter 200 are moved toward the proximal side of the second instrument 120 and are pulled out from the second instrument 120. Since the proximal end opening portion 124a of the second instrument 120 is formed to have an obliquely cut shape (refer to FIG. 3B), the guide member 300 and the catheter 200 can be easily pulled out from the second instrument 120 by moving the guide member 300 and the catheter 200 toward the proximal side along the shape of the larynx 450 positioned on a side above the trachea 440.

Subsequently, as illustrated in FIG. 10A, the main body portion 121 of the second instrument 120 is thrust into the esophagus 430 at the distal end of the catheter 200 (arrow p in the diagram). In the second instrument 120, since the outer diameter of the proximal portion 124 is formed to be smaller than that of the distal portion 123 (refer to FIG. 3B), the proximal portion 124 can be favorably prevented from coming into contact with the inner wall of the esophagus 430 and the like when being thrust into the esophagus 430.

Subsequently, the inserting step (S20) and the interlocking step (S30) are performed.

As illustrated in FIG. 10B, the proximal portion 124 of the second instrument 120 is inserted into the proximal end opening portion 114a of the first instrument 110. Then, the first instrument 110 and the second instrument 120 are interlocked with each other by the first magnet 117 of the first instrument 110 and the second magnet 127 of the second instrument 120.

According to the above-described process, the first instrument 110 can indwell in the esophagus 430 and the second instrument 120 can indwell in the larynx 450 and the trachea 440. Moreover, the main body portion 121 of the second instrument 120 can indwell across from the larynx 450 to the esophagus 430.

The first instrument 110 indwelling in the esophagus 430 allows food, saliva, or the like to move to the stomach via the esophagus 430 through the lumen 115 of the first instrument 110. Arrival of gastric juice or the like flowing backward from the stomach to the larynx 450 which is a bifurcated portion between the esophagus 430 and the trachea 440 is suppressed due to the resistance of the wall face of the lumen 115. Particularly, in the first instrument 110, gastric juice or the like can be favorably prevented from flowing backward along the wall surface of the lumen 115, due to the spiral projection portion 115a formed on the inner surface of the lumen 115.

The second instrument 120 indwelling in the larynx 450 and the trachea 440 allows gas such as air passing through the larynx 450 and the trachea 440 to circulate and substantially narrows the circulation route (the diameter of trachea 440 or the diameter near the larynx 450) of food or saliva. When the diameter of the trachea 440 or the diameter near the larynx 450 is partially narrowed, even in a case where pulmonary aspiration occurs, it is possible to suppress food or saliva from invading a lung via the larynx 450 and the trachea 440. Particularly, in the second instrument 120, the main body portion 121 is inserted into the lumen 115 of the first instrument 110 and indwells across an area from the larynx 450 to the esophagus 430. Since the main body portion 121 inhibits food, saliva, or the like from flowing down in the route toward the trachea 440 side, pulmonary aspiration can be effectively prevented from occurring.

The first instrument 110 and the second instrument 120 can be detached from a living body and can be appropriately evulsed out from the living body after indwelling in the living body for a desired period of time. During the evulsion, for example, the work can promptly proceed by utilizing the image-capturing means such as an endoscope.

In embodiments herein, the treatment example in which the second instrument 120 indwells in both the larynx 450 and the trachea 440 has been described. Note that, in a case where the object is to prevent aspiration pneumonitis, the configuration is acceptable as long as the second instrument 120 is disposed in at least the larynx 450. In addition, the second instrument 120 can indwell on the oral cavity side closer than the vocal cord. When the second instrument 120 indwells on the oral cavity side closer than the vocal cord, it is possible to suppress food, saliva, or the like from invading a lung and to prevent the vocal cord from being blocked by the second instrument 120. Therefore, it is possible to prevent hindrance to vocalization and the like caused by the indwelling of the second instrument 120. In addition, it is preferable that the second instrument 120 indwells to avoid the place near the epiglottis, for example, in a case of a patient having a weakened epiglottis. Accordingly, pathogenesis of epiglottitis or the like can be favorably prevented.

As described above, the treatment method (that is, the method of preventing aspiration pneumonitis) includes the disposing step (S10) of disposing the first instrument 110, which allows the object that becomes a causative agent of aspiration pneumonitis to move from the esophagus 430 to the stomach and suppresses movement of the object from the stomach to the larynx 450, in the esophagus 430 and disposing the second instrument 120, which suppresses the object from invading the lung, in at least the larynx 450.

According to the above-described treatment method, due to the first instrument 110 disposed in the esophagus 430, gastric juice or the like can be prevented from flowing backward from the stomach to the larynx 450. Moreover, due to the second instrument 120 disposed in the larynx 450, pulmonary aspiration of food, saliva, or the like invading a lung via the larynx 450 and the trachea 440 can be prevented from occurring. Therefore, pathogenesis of aspiration pneumonitis can be favorably prevented.

In addition, the disposing step (S10) includes the first indwelling step (S11) of inserting the catheter 200, which is provided with the lumen 215 accommodating the first instrument 110 and the second instrument 120 in order from the distal portion side, into the esophagus 430 and releasing the first instrument 110 in the esophagus 430 to indwell the first instrument 110 in the esophagus 430, the second indwelling step (S12) of inserting the catheter 200 into the larynx 450 and releasing the second instrument 120 in the larynx 450 to indwell the second instrument 120 in the larynx 450, and the extending step (S13) of causing the second instrument 120 to extend across from the larynx 450 to the esophagus 430.

Therefore, low invasive procedure can be realized by utilizing the catheter 200. In addition, when the second instrument 120 is disposed across from the larynx 450 to the esophagus 430, pulmonary aspiration can be more effectively prevented from occurring. Moreover, since the second instrument 120 indwells in the larynx 450 and the trachea 440 after the first instrument 110 indwells in the esophagus 430, stimulation applied to each of the receptors and causing protective defense for the respiratory tract can be suppressed as much as possible. Accordingly, a burden applied to a patient can be reduced while the first instrument 110 and the second instrument 120 are indwelled. Thus, lower invasive procedure can be realized.

In addition, the first instrument 110 has the hollow main body portion 111 and the first expansion portion 116 which is expandingly deformed in response to release from the lumen 215. The second instrument 120 has the hollow main body portion 121 and the second expansion portion 126 which is expandingly deformed in response to release from the lumen 215. Then, in the first indwelling step (S11), the release of the first instrument 110 from the lumen 215 causes the first expansion portion 116 to be expandingly deformed and the first instrument 110 to indwell in the esophagus 430. Moreover, in the second indwelling step (S12), the release of the second instrument 120 from the lumen 215 causes the second expansion portion 126 to be expandingly deformed and the second instrument 120 to indwell in the larynx 450.

Therefore, the first instrument 110 can indwell in the esophagus 430 and the second instrument 120 can indwell in the larynx 450 through simple work of releasing each of the first expansion portion 116 and the second expansion portion 126 from the lumen 215 of the catheter 200.

In addition, the embodiments can have the inserting step (S20) of inserting the main body portion 121 of the second instrument 120 into the main body portion 111 of the first instrument 110, and the interlocking step (S30) of interlocking the first instrument 110 and the second instrument 120 with each other. The inserting step (S20) and the interlocking step (S30) are performed after the extending step (S13).

Therefore, the interlocking state between the first instrument 110 and the second instrument 120 can be favorably maintained, and thus, pulmonary aspiration with respect to a lung can be favorably prevented from occurring.

In addition, in the disposing step (S10), the first instrument 110 is disposed while the image-capturing means (for example, an endoscope) captures an image of the inside of the esophagus 430, and the second instrument 120 is disposed while the image-capturing means captures an image of the inside of the larynx 450.

Therefore, work of disposing the first instrument 110 and the second instrument 120 can promptly and easily proceed.

In addition, the medical apparatus 100 can include the first instrument 110 that is disposed in the esophagus 430 to allow the object that becomes a causative agent of aspiration pneumonitis to move from the esophagus 430 to the stomach and to suppress movement of the object from the stomach to the larynx 450, and the second instrument 120 that is disposed in at least the larynx 450 to suppress the object from invading a lung.

According to the above-described medical apparatus 100, gastric juice or the like can be prevented from flowing backward from the stomach to the larynx 450 by disposing the first instrument 110 in the esophagus 430. Moreover, pulmonary aspiration of food, saliva, or the like invading a lung via the trachea 440 can be prevented from occurring by disposing the second instrument 120 in the larynx 450. Therefore, pathogenesis of aspiration pneumonitis can be favorably prevented.

In addition, the medical apparatus 100 can have the catheter 200 that is provided with the lumen 215 in which the first instrument 110 and the second instrument 120 are accommodated in order from the distal portion side. Then, the first instrument 110 has the hollow main body portion 111 and the first expansion portion 116 which is expandingly deformed in response to release from the lumen 215, and the second instrument 120 has the hollow main body portion 121 and the second expansion portion 126 which is expandingly deformed in response to release from the lumen 215. Therefore, the first instrument 110 can indwell in the esophagus 430 and the second instrument 120 can indwell in the larynx 450 through simple work of releasing each of the first expansion portion 116 and the second expansion portion 126 from the lumen 215 of the catheter 200.

In addition, in the medical apparatus 100, the catheter 200 can have the guide lumen 235 through which the guide member 300 guiding delivery to the esophagus 430 and the larynx 450 can be inserted. Therefore, indwelling work can be performed while the endoscope or the guide wire is utilized as the guide member 300. Thus, prompt and easy procedure can be realized.

In addition, in the medical apparatus 100, the second instrument 120 can be disposed across from the larynx 450 to the esophagus 430. Accordingly, pulmonary aspiration can be more effectively prevented from occurring.

In addition, the medical apparatus 100 can have the interlocking means 130 that interlocks the first instrument 110 disposed in the esophagus 430 and the second instrument 120 disposed in the larynx 450 with each other. Therefore, the interlocking state between the first instrument 110 and the second instrument 120 can be favorably maintained, and thus, pulmonary aspiration with respect to a lung can be favorably prevented from occurring.

Hereinbefore, the treatment method and the medical apparatus have been described through the embodiments above. Note that, the embodiments herein are not limited to only the method and the apparatus described above but can be suitably changed based on the disclosed Claims.

For example, the procedure can proceed indwelling the second instrument in the larynx and then, indwelling the first instrument in the esophagus. In addition, the first instrument and the second instrument may be indwelled without using the catheter described, and each of the instruments may be indwelled by using apparatuses different from each other.

In addition, for example, the configuration and the like of the first instrument are not particularly limited as long as the first instrument indwells in the esophagus and has the function of allowing food or the like to move from the esophagus to the stomach and suppressing back-flow of foreign bodies from the stomach to the larynx. Similarly, the configuration and the like of the second instrument are not particularly limited as long as the second instrument indwells in at least the larynx and has the function of suppressing food, saliva, or the like from invading a lung. For example, the second instrument does not have to be disposed to extend toward the esophagus side. In addition, the first expansion portion provided in the first instrument and the second expansion portion provided in the second instrument do not have to have the self-expandable-type structure as described in the embodiment. For example, the first expansion portion and the second expansion portion can be configured to be expandingly and contractibly deformed through a mechanical operation.

The configuration of the catheter is not limited to the illustrated structure and the like. For example, the structures of the hand operation unit and other units can be suitably changed. In the description of the embodiments above, a rapid exchange-type catheter device is illustrated as the catheter. However, the type of the catheter is not particularly limited. For example, an over-the-wire-type catheter device may be adopted.

REFERENCE SIGNS LIST

100 MEDICAL APPARATUS,
110 FIRST INSTRUMENT,
111 MAIN BODY PORTION (FIRST MAIN BODY PORTION),
115 LUMEN,
115a PROJECTION PORTION,
116 FIRST EXPANSION PORTION,
117 FIRST MAGNET,
120 SECOND INSTRUMENT,
121 MAIN BODY PORTION (SECOND MAIN BODY PORTION),
125 LUMEN,
126 SECOND EXPANSION PORTION,
127 SECOND MAGNET,
130 INTERLOCKING MEANS,
200 CATHETER,
211 SHAFT,
215 LUMEN,
230 INNER SHAFT,
235 GUIDE LUMEN,
300 GUIDE MEMBER,
410 ORAL CAVITY,
420 PHARYNX,
430 ESOPHAGUS,
440 TRACHEA, AND
450 LARYNX.

What is claimed is:

1. A treatment method for preventing an object that becomes a causative agent of aspiration pneumonitis from invading a lung, the treatment method comprising:
  disposing a first instrument, which allows the object to move from an esophagus to a stomach and suppresses movement of the object from the stomach to a larynx, in the esophagus;
  disposing a second instrument, which suppresses the object from invading the lung, in at least the larynx;
  wherein disposing the first and second instruments comprises:
    inserting a catheter, which is provided with a lumen accommodating the first instrument and the second instrument in order from a distal portion side, into the esophagus;
    releasing the first instrument in the esophagus to indwell the first instrument in the esophagus;
    inserting the catheter into the larynx;
    releasing the second instrument in the larynx to indwell the second instrument in the larynx; and
    causing the second instrument to extend across from the larynx to the esophagus;
  wherein the first instrument has a hollow first main body portion and a first expansion portion which is expandingly deformed in response to being released from the lumen, wherein the second instrument has a hollow second main body portion and a second expansion portion which is expandingly deformed in response to being released from the lumen, wherein in indwelling the first instrument, releasing the first instrument from the lumen causes the first expansion portion to be expandingly deformed and indwells the first instrument in the esophagus, and wherein in indwelling the second instrument, releasing the second instrument from the lumen causes the second expansion portion to be expandingly deformed and indwells the second instrument in the larynx;

inserting the second main body portion of the second instrument into the first main body portion of the first instrument; and interlocking the first instrument and the second instrument with each other, wherein inserting and interlocking are performed after extending the second instrument.

2. The treatment method according to claim 1, wherein in disposing the first instrument, the first instrument is disposed while image-capturing means captures an image of an inside of the esophagus, and the second instrument is disposed while the image-capturing means captures an image of an inside of the larynx.

3. The treatment method according to claim 1, wherein interlocking the first instrument disposed in the esophagus and the second instrument disposed in the larynx with each other comprises magnetically coupling a first magnet of the first instrument with a second magnet of the second instrument.

4. The treatment method according to claim 1, wherein interlocking the first instrument and the second instrument with each other comprises pushing a proximal portion of the second instrument into the first instrument.

5. The treatment method according to claim 1, wherein the catheter is inserted through an oral cavity.

\* \* \* \* \*